(12) United States Patent
Lehmann

(10) Patent No.: US 8,309,520 B2
(45) Date of Patent: Nov. 13, 2012

(54) FULLY SYNTHETIC ALBUMIN ANALOG

(75) Inventor: Hans-Dieter Lehmann, Bisingen-Zimmern (DE)

(73) Assignee: LS MedCap GmbH, Hechingen (DE)

( * ) Notice: Subject to any disclaimer, the term of this patent is extended or adjusted under 35 U.S.C. 154(b) by 0 days.

(21) Appl. No.: 12/952,629

(22) Filed: Nov. 23, 2010

(65) Prior Publication Data

US 2011/0117139 A1  May 19, 2011

Related U.S. Application Data

(63) Continuation of application No. PCT/EP2009/003651, filed on May 22, 2009.

(30) Foreign Application Priority Data

May 30, 2008 (DE) .......... 10 2008 027 133

(51) Int. Cl.
- A61K 38/38 (2006.01)
- A61K 47/00 (2006.01)
- C07K 14/76 (2006.01)
- C07K 17/00 (2006.01)

(52) U.S. Cl. .......... 514/15.2; 514/776; 530/362

(58) Field of Classification Search .......... 514/15.2, 514/776; 530/362
See application file for complete search history.

(56) References Cited

U.S. PATENT DOCUMENTS

| | | | |
|---|---|---|---|
| 5,871,713 A | 2/1999 | Meyer et al. | |
| 6,294,186 B1 * | 9/2001 | Beerse et al. | 424/405 |
| 6,448,254 B1 | 9/2002 | Lubisch et al. | |
| 6,670,199 B2 | 12/2003 | Caldwell et al. | |
| 7,005,414 B2 | 2/2006 | Barnikol et al. | |
| 2002/0019037 A1 | 2/2002 | Caldwell et al. | |
| 2003/0215419 A1 | 11/2003 | Guire et al. | |
| 2004/0142011 A1 | 7/2004 | Nilsson et al. | |
| 2004/0234575 A1 | 11/2004 | Horres et al. | |
| 2005/0176678 A1 | 8/2005 | Horres et al. | |
| 2006/0015057 A1 | 1/2006 | Ho et al. | |
| 2006/0041023 A1 | 2/2006 | DeGrado et al. | |
| 2007/0202342 A1 * | 8/2007 | Whiteford et al. | 428/425.5 |
| 2008/0131583 A1 | 6/2008 | Nakel et al. | |

FOREIGN PATENT DOCUMENTS

| | | |
|---|---|---|
| DE | 10261986 | 5/2002 |
| DE | 10329296 | 6/2003 |
| FR | 2665902 | 2/1992 |
| WO | 93/10824 | 6/1993 |
| WO | 99/54294 | 10/1999 |
| WO | 02/00230 | 1/2002 |
| WO | 03/094991 | 11/2003 |
| WO | 2005/002640 | 1/2005 |
| WO | 2007/019994 | 2/2007 |
| WO | WO 2009/146803 | * 12/2009 |

OTHER PUBLICATIONS

Winblade et al., 2002, "Sterically blocking adhesion of cells to biological surfaces with a surcease-active copolymer containing poly-(ethylene glycol) and phenylboronic acid", Journal of Biomedical Materials Research, Wiley, NY, 59 (4):618-631.

* cited by examiner

Primary Examiner — Amber D. Steele
(74) Attorney, Agent, or Firm — Casimir Jones SC

(57) ABSTRACT

The present invention relates to a fully synthetic albumin analog, to a hemocompatible coating for medical devices containing the fully synthetic albumin analog, as well as to medical devices coated with the hemocompatible coating. The albumin analog preferably has two basic structures which are connected with one another via at least one bridging unit, the basic structures respectively having, in a geometrically defined manner, at least two bound joint regions to which at least one residue is covalently bound, wherein the basic structures are, respectively, a benzene carboxylic acid, and wherein the joint regions are formed via acid amide bonds, and wherein each residue, respectively, comprises a lipophilic region and a hydrophilic region.

5 Claims, 4 Drawing Sheets

| | n= |
|---|---|
| Monomer PEO 350 | 8 |
| Monomer PEO 550 | 12-13 |
| Dimer PEO 350 | 8 |

FULLY SYNTHETIC ALBUMIN ANALOG

CROSS REFERENCE TO RELATED APPLICATIONS

This application is a continuation of international patent application PCT/EP2009/003651, filed on May 22, 2009 designating the U.S., which international patent application has been published in German language and claims priority from German patent application DE 10 2008 027 133.0, filed on May 30, 2008. The entire contents of these priority applications are incorporated herein by reference.

BACKGROUND OF THE INVENTION

The present invention relates to a compound which is usable in coatings for surfaces which come into contact with blood, in order to improve the hemocompatibility of the surface, and also to a coating of this kind and a medical device having at least one surface of this kind.

Compounds of this kind, coating compositions, and also methods for coating surfaces of medical devices are well known in the prior art.

In many medical treatments, use is made of medical devices of this kind which have plastics surfaces which come into contact with the blood of a patient over longer or shorter periods of time. These devices are, for example, disposable equipment for a heart-lung machine, oxygenators, dialyzers, ultrafilters, catheters, artificial organs such as heart or kidney, gas exchange membranes, or vascular prostheses, and this list is not to be understood as conclusive.

With all this medical equipment, the contact of blood which takes place with hydrophobic polymer surfaces activates various defense mechanisms in the blood. This is particularly true when conducting blood through dialyzers or ultrafilters which have hydrophilic membranes, but also when conducting blood through oxygenators having hydrophobic membranes and having large areas of defoamers, with the presence here of far higher flow velocities of the blood.

Here, not only the current-induced trauma but also, in particular, the properties of the plastics surfaces themselves are responsible for undesired reactions in the blood.

Adhesion of blood constituents to plastics surfaces and coagulation can occur, and this increases, firstly, the risk of malfunction of the equipment and, secondly, the risk of thrombosis. Furthermore, there occurs mainly an activation of blood constituents of the immune system, more particularly the complement system. Such an activation of the immune response is, however, disadvantageous, more particularly in view of the compromised health of the patients, and should therefore be prevented.

Therefore, for medical equipment and accessories which come into contact with blood, it is desirable to have available plastics surfaces which have a good blood compatibility.

Good blood compatibility, i.e. hemocompatibility, is generally understood to mean the property of a surface or substance such that the surface, upon contact with blood, activates neither blood coagulation nor the defense mechanisms of the body against the foreign surface or substance.

In order to achieve this, it is known to coat the plastics surfaces which come into contact with blood in such a way that these surfaces have an improved hemocompatibility.

It should be noted that, for example, dialyzer casings, oxygenators, and corresponding accessories are preferably made from clear polycarbonate, whose transparency and appearance must not be compromised by hydrophilizing coatings of this kind. It should be further noted that coatings of this kind are carried out before the sterilization of the corresponding medical equipment in order to reduce blood trauma during the use of industrially ready-made equipment. This is important against the background of there being a need for blood-compatible and sterile medical devices which can be kept in stock and are ready to use at any time and, in particular, in case of emergency.

In this connection, it is known, for example, to inhibit blood coagulation by a high-dose administration of heparin, or else to bind heparin to such surfaces which come into contact with blood.

It is further known to achieve a certain hemocompatibility of plastics surfaces by prerinsing with patients' blood or by coating with blood constituents of human, animal, or biotechnological origin.

Here, it is, in particular, albumin, which is a protein present in large amounts in the blood and which is rapidly adsorbed by the hydrophobic surfaces and then denatured on these surfaces, whereby the surfaces become hydrophilized.

It is further known to improve the hemocompatibility in or on medical equipment and/or accessories by coating plastics surfaces with synthetic surfactants.

However, the methods described in this respect all have certain disadvantages.

The inhibition of blood coagulation by means of heparin is contraindicated particularly in emergency medicine and especially in patients who may have mechanical or chemical traumas, since greater bleeding can occur as a result.

In the case of prerinsing with patients' blood, it is particularly disadvantageous that the coating can only be carried out immediately before the use of the devices to be thus coated. Thus, valuable time would be lost in emergency treatments, and this could lead to a considerable negative impact on the health of the patient. Furthermore, this treatment has the disadvantage that it can only be used within a very narrow time frame. Since the albumin taken up by the lipophilic surfaces during prerinsing of the device with patients' blood is easily displaced from said surfaces by other lipophilic substances, a continuous worsening of the hemocompatibility occurs.

Also, the denaturation of albumin at the lipophilic surfaces can lead to increased release of lipophilic substances bound to the albumin, such as medicaments or toxins, whereby the effects of medicaments used become more difficult to judge and toxic effects can occur. Furthermore, it is not possible with this method to control the coating quality.

In the case of coating with blood constituents of human or animal origin, more particularly the risk of infection is a factor which greatly impedes official approval of coatings of this kind. Furthermore, incompatibility reactions can occur in coatings of this kind.

Coating with constituents acquired by biotechnological methods is, in contrast, particularly disadvantageous because of the costs arising in connection with the acquisition and purification of these substances.

In order to address these problems and also the problems of approval with regard to albumin coatings, there is therefore a need for physiologically safe, novel coating materials for the hydrophilization of polymer surfaces, where the absence of viruses and other biological risk factors can also be assumed.

For the hemocompatible coating of plastics surfaces, use is therefore increasingly made of synthetic substances such as polymers or surfactants.

In this connection, U.S. Pat. No. 6,670,199 describes various coatings which comprise, as a basic structure, the surfactant Pluronic™, which can be conjugated with different biomolecules.

WO 2007/01994 showed that, although these coatings have antithrombogenic properties, they also result at the same time in a large deterioration in complement activation. The known coating thus does not have good blood compatibility. Furthermore, it has the disadvantage that the evenness of the coating is difficult to control.

A further requirement for coating methods is that, during operation of the medical equipment provided with correspondingly coated surfaces, leaching of coating material from the coated surfaces must not occur. Such a leaching might, in particular, induce toxic effects, such as the triggering of inflammatory reactions for example, after recirculation of the blood into the bloodstream of the patient.

It is known that synthetic substances in blood are almost always perceived as foreign and trigger defense mechanisms. The bonding of polyethylene oxide groups (PEO) to foreign molecules of this kind has a masking effect and is thus able to suppress immunological defense reactions. In this connection, WO 2007/019994 A1 discloses the use of certain ester surfactants in hemocompatible coatings of lipophilic surfaces. These ester surfactants have up to six long-chain fatty acid residues to which polyethylene oxide chains are bound. Because of these bound PEO radicals, the surfactants are soluble in water.

The immunological masking by PEO groups is also used in the production of artificial blood from hemoglobin of animal origin, as disclosed in, for example, WO 2002/000230 A1. For this purpose, exogenous substances are masked by attaching polyethylene oxide chains, whereby the triggering of the immune response can be reduced.

From the above-mentioned WO 2007/019994 A1, it is known that a reduced complement activation compared with Pluronic™ can be achieved using one of the ester surfactants described, which is sold as Cremophor™, owing to the combination of a large lipophilic molecular moiety, which allows a relatively strong adhesion to lipophilic surfaces via van der Waals forces, with attached PEO chains, which mask the substance from the components of the immune response.

In house comparative experiments have shown, however, that changes occur even in blood which comes into contact with Cremophor™-coated surfaces, compared with identical human blood which has not been exposed to surfaces, which changes indicate a strong activation of components of the immune system.

Against this background, an object of the present invention is therefore to provide a new class of compounds which can be used in coatings for surfaces which come into contact with blood and which have improved hemocompatible properties compared with known compounds.

SUMMARY OF THE INVENTION

According to the invention, this and other objects are achieved by providing a fully synthetic albumin analog having two basic structures which are connected with one another via at least one bridging unit, the basic structures respectively having, in a geometrically defined manner, at least two bound joint regions to which at least one residue is covalently bound, wherein the basic structures are, respectively, a benzene carboxylic acid, and wherein the joint regions are formed via acid amide bonds, and wherein each residue, respectively, comprises a lipophilic region and a hydrophilic region.

It has been found within the context of the present invention, that with the novel albumin analogs in coatings, the hemocompatibility of, e.g., plastics surfaces which come into contact with blood is distinctly improved compared with the coating substances and methods known in the prior art.

Against this background, the present invention also relates to a hemocompatible coating for surfaces which come into contact with blood, said coating comprising at least one novel fully synthetic albumin analog.

The present invention further relates to a medical device having at least one surface of this kind, and also to the use of the novel albumin analog in a coating for polymer surfaces which come into contact with blood.

The novel albumin analog has the advantage that a lipophilic molecular moiety can be achieved by the three-dimensional basic structure used according to the invention, which moiety has a higher spatial density than known substances in which linear aliphatic compounds are used as linkers.

This leads, firstly, to a stronger van der Waals interaction of the novel albumin analogs with lipophilic surfaces and thus to an improved adhesion; however, it also promotes solubility in an aqueous medium owing to the lower space requirement of the lipophilic molecular moiety.

The good solubility in an aqueous medium is advantageous because stress corrosion cracking can occur when coating plastics surfaces with coating agents comprising organic solvents.

The joint regions define the spatial arrangement of the residues covalently bound thereto and thus offer the advantage that an organized distribution pattern of the hydrophilic molecular moieties on the surface emerges during adhesion of the novel compound to a lipophilic surface.

Thus, a homogeneous occupation of the surface with molecular moieties mediating hemocompatibility can be achieved using the novel albumin analog, this not being possible or known with known substances having a spatially undefined basic structure.

All this leads to a substantial improvement of the coating quality and, at the same time, a reduced amount of the coating substances to be used, when using the novel albumin analog.

Three different exemplary embodiments of the novel albumin analog were tested in-house in the Chandler loop test with respect to their hemocompatible properties and compared with the properties of Cremophor®EL. Here, the novel albumin analogs showed themselves to be superior to the known Cremophor®EL, more particularly in respect of the platelet number and thromboglobulin concentration which were detected in the tested blood after the exposure and which represent a measure of the activation of the immune system.

The inventor has further found that the novel albumin analog is excreted by the kidneys and can therefore be eliminated from patients' blood via the kidneys, in contrast to human albumin.

Against this background, the present invention also relates to the use of the novel albumin analog for intracorporeal detoxification.

The novel compound is referred to as an albumin analog because it, like human albumin, is present in a colloidal form in blood and in aqueous solutions. It has hydrophilic and hydrophobic regions. The hydrophilic regions determine the solubility in water, whereas the hydrophobic portions, in solution, are present in the interior of the molecular ellipsoid and form pockets in which lipophilic substances can be transported, for example hydrophobic medicaments or, in the case of hepatitis, bilirubin.

The novel albumin analogs have in particular very high affinities to hydrophobic substances and are excreted by the kidneys even as a toxin-loaded complex. As a result, by adding a substance according to the invention, there is provided the opportunity of binding toxic lipophilic substances present in blood in a complex and excreting them via the kidneys.

For the novel albumin analog, preference is given to selecting the three-dimensional basic structure from the group comprising simple aromatic systems, fused aromatic systems, simple heteroaromatic systems, fused heteroaromatic systems, and hydrogenation products of the abovementioned substance classes.

Here, it is advantageous that monocyclic or polycyclic compounds of this kind have a defined three-dimensional structure which achieves, in the albumin analog according to the invention, an advantageous organization of the basic structures and residues and also a high spatial density of lipophilic molecular moieties.

In the case of fused aromatic systems, simple heteroaromatic systems, and/or fused heteroaromatic systems, an essentially planar geometry is present, and an ideal contact area for the formation of van der Waals interactions with lipophilic surfaces is therefore formed in the cooperation of the basic structures with the lipophilic portions of the residues bound thereto.

In the case of the hydrogenation products of aromatic systems or heteroaromatic systems, an advantageous effect results, firstly, from the possibility of bonding joint regions at defined positions, either axially or equatorially to the basic structures, whereby spatially organized molecular moieties which have a different function can be achieved by, for example, a differential occupation of axial or equatorial joint regions with lipophilic or hydrophilic residues. Secondly, an advantageous effect results from the relative flexibility of a hydrogenated ring structure which, while simultaneously and substantially maintaining a defined alignment, allows an efficient adhesion and van der Waals interaction even with strongly structured polymer surfaces.

In a development, preference is given to the at least one residue having inner regions which are bound to the joint regions and having outer regions which are bound to the inner regions.

Here, it is advantageous that the inner and outer regions, which have different properties with respect to, for example, their hydrophilicity, can form shapes, for example a core and a coat, by rearrangement or assembly. These shapes, in turn, can interact with various media or surfaces in an energetically preferred manner with respect to, for example, their hydrophilicity.

Preference is given to the inner regions having lipophilic regions and the outer regions having hydrophilic regions.

For compounds present in solution in an aqueous medium, it is advantageous here that the lipophilic regions arranged internally are shielded from the surrounding medium by the hydrophilic regions arranged externally, leading to an increased solubility.

For compounds associated with a lipophilic surface, it is, in contrast, advantageous that the lipophilic regions of the basic structure and of the residues lie close together, i.e., form a continuous lipophilic molecular moiety, allowing an efficient van der Waals interaction with the lipophilic surface.

Preference is given to the lipophilic regions being formed by alkyl chains, which form a strong van der Waals interaction with lipophilic surfaces.

Furthermore, preference is given to hydrophilic regions being formed by polyethylene oxide chains (PEO), which have hydrophilic properties which allow a good water solubility of the novel albumin analogs and the formation of a hydrophilic contact area having an antithrombogenic and hemocompatible effect.

Furthermore, PEO chains are, as described in the above-mentioned WO 2002/000230 A1, suitable for masking foreign substances from the immune system and thus reducing the triggering of the immune response.

Furthermore, the alkyl chains act to additionally enlarge the lipophilic molecular moiety in order to strengthen the binding of the novel albumin analogs to lipophilic surfaces. The PEO chains, in contrast, mediate the solubility in an aqueous medium, for example in a coating solution, so that a coating can be applied to a surface by rinsing.

Furthermore, preference is given to saturating a chain terminal on residues with organic radicals.

Since terminal hydroxyl groups contribute to the activation of the complement system, it is advantageous here that a chain end generated by saturation with an organic radical, for example by a methoxyl group or by acetylation, and which, when in contact with blood, induces little or no triggering of the complement response.

In one development, preference is given to residues being connected with one another by at least one bridge.

Here, it is advantageous that, in addition to the spatial organization of the residues via the basic structures, a further increased degree of spatial organization of the residues to one another is generated by bridges.

Here, care should then be taken that the solubility in aqueous media, the adhesion to lipophilic surfaces, and the rearrangement process during adhesion of molecules present in solution to a lipophilic surface are not significantly reduced or impeded by the introduced spatial definition of the residues to one another which was.

In one embodiment of the novel albumin analogs, preference is given to the analog having at least two basic structures which are connected with one another via at least one bridging unit.

Here, it is advantageous that the degree of spatial or planar organization can be further increased via the connection of multiple basic structures with one another. This leads to a further rise in coating quality.

Furthermore, analogous to protein structures such as albumin for example, the solubility in an aqueous medium can be further improved and, at the same time, the formation of aggregates from multiple molecules can be counteracted by assembling the lipophilic molecular moieties in the interior of the molecule.

In addition, the number of residues in the entire molecule bound to the basic structures can also be varied via the number of basic structures connected to one another by a bridging unit.

Furthermore, preference is given to the bridging unit having an alkyl bridge of the formula $(CH_2)_n$ having a length of n=2 to 18.

It is advantageous that a larger contiguous lipophilic molecular moiety can be achieved by means of an alkyl bridge between two basic structures, and this in turn increases the formation of van der Waals interactions.

Furthermore, preference is given to the bridging unit having at least one branch to which a residue is bound.

Here, it is advantageous that the lipophilic molecular moiety can be further enlarged via, for example, the introduction of a lipophilic branch on the bridging unit.

Furthermore, at a single- or multiple-branched bridging unit, it is possible to introduce hydrophilic residues, such as PEO chains for example, which increase the solubility and hemocompatibility of the molecule through the improved shielding of the lipophilic molecular moiety from the aqueous medium or blood.

According to a development of the novel albumin analogs, preference is given to introducing hydrophilic functions, for example ionic groups such as carboxylate, phosphate, or sulfonate anions, at some joint regions, residues, and/or bridging units.

Here, it is advantageous that the introduction of ionic groups facilitates the control of the quality of a coating with the novel albumin analogs. Thus, anionic groups can be introduced which are stained with cationic dyes for control purposes and then detected visually or automatically.

In summary, the novel albumin analogs which come into use in an aqueous solution or emulsion have the advantage that they can have a high lipophilic proportion and are nevertheless suitable for coating by means of aqueous media. In an aqueous medium, the lipophilic regions are completely shielded by the hydrophilic regions. On lipophilic plastics surfaces, the lipophilic portion of the novel albumin analogs unfolds in a suitable manner so that it adheres well via van der Waals interactions to the surfaces to be coated. This unfolding is caused by suitable joint regions which allow the spatial rearrangement.

Against the background of the above embodiments, a hemocompatible coating for surfaces which come into contact with blood can have at least one fully synthetic albumin analog.

This hemocompatible coating can—as already mentioned—be applied to lipophilic surfaces, of medical devices for example, which come into contact with blood and can give them good hemocompatible and antithrombogenic properties. As a result, the activation of the complement system in blood is attenuated and adsorption and coagulation of erythrocytes or leukocytes on the surfaces is counteracted.

Preference is given to the hemocompatible coating having one or more hemocompatible, detectable substances.

Here, it is advantageous that, in the course of the quality assurance, the coating quality of each individual medical apparatus produced which has a coating according to the invention can be checked without the need for additional methods, such as rinsing with a liquid comprising a detectable substance for example.

At the same time, the further advantageous properties of the coating, more particularly the hemocompatibility, are retained.

A medical device having at least one plastics surface made of polycarbonate, polyethylene, polypropylene, polymethylpentene, polyurethane, polyester, silicone, hard or soft polyvinyl chloride, copolymers such as, for example, acrylonitrile butadiene styrene copolymer, ethylene propylene (diene) copolymer, etc. can be coated according to the invention with the novel albumin analogs.

Preference is given here to the medical device being a component of disposable equipment of a heart-lung machine, of an oxygenator, of a catheter, of an artificial heart, of an artificial kidney, of a gas exchange membrane, or of a vascular prosthesis.

Further advantages are evident from the appended description and the tables.

It will be appreciated that the features mentioned above and yet to be explained below can be used not only in the combinations indicated in each case but also in other combinations or alone, without departing from the scope of the present invention.

DESCRIPTION OF PREFERRED EMBODIMENTS

Figure 1:
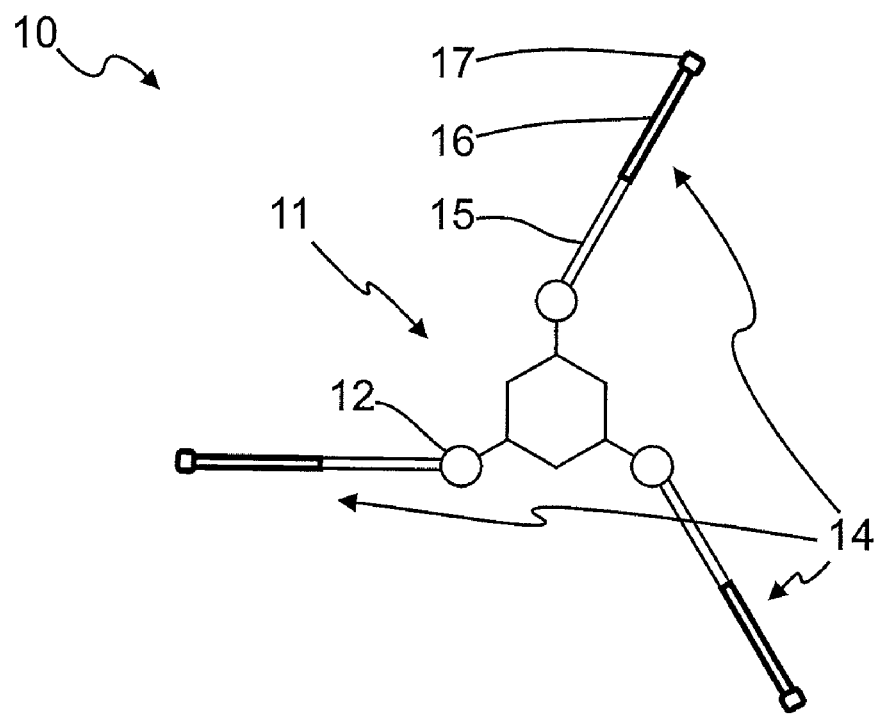
FIG. 1 shows a diagrammatic illustration of a possible embodiment of the novel albumin analogs having externally arranged hydrophilic molecular moieties.

FIG. 1 depicts a diagrammatic illustration of a possible embodiment of the novel albumin analogs 10. Here, residues 14 are covalently bound to a three-dimensional basic structure 11 via joint regions 12. These residues 14 each have an inner region 15, an outer region 16, and a chain terminal 17, wherein the inner region 15 has lipophilic characteristics; whereas the outer region 16 and the chain terminal 17 have hydrophilic characteristics.

In this figure and the following figures, hydrophilic molecular moieties of the residues are identified by a thick line. The molecular constituents depicted multiple times, such as joint regions 12 for example, are, by way of example only, provided with reference symbols in the drawing for reasons of clarity.

This embodiment has the advantage of an altogether compact molecular structure, wherein the residues are arranged radially symmetrically and in a planar manner on the basic structure. Thus, a high degree of organization is achieved at surfaces. In solution, in contrast, a good compacting of the lipophilic molecular moiety and an efficient hydrophilic coating are achieved by rearrangement of the residues.

Figure 2:
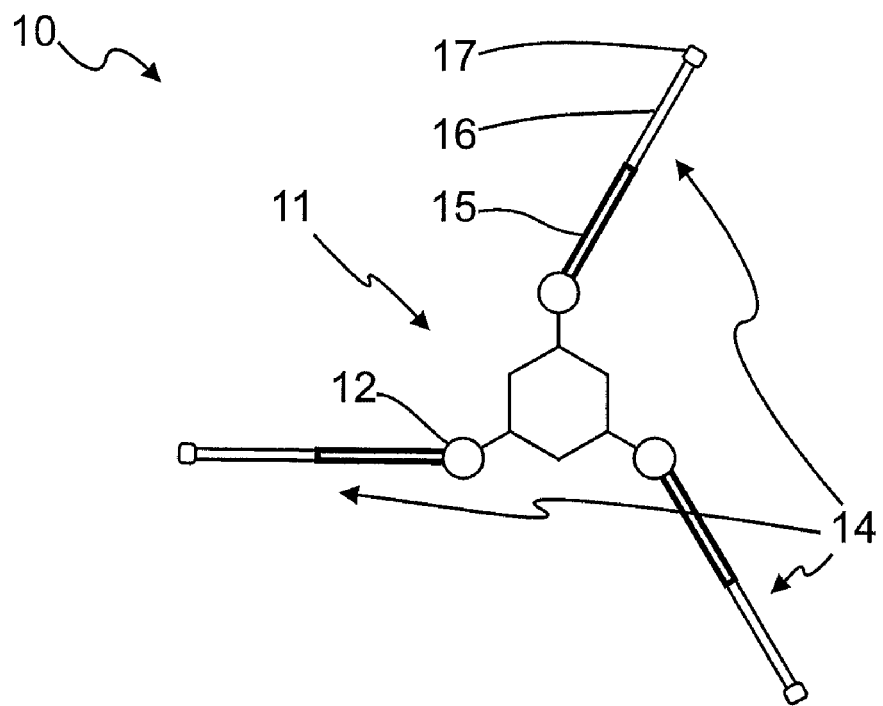
FIG. 2 shows a diagrammatic illustration of a possible embodiment of the novel albumin analogs having externally arranged lipophilic molecular moieties.

The embodiment depicted in FIG. 2 largely corresponds to the embodiment in FIG. 1. However, in this case, the outer region 16 and the chain terminal 17 of the residues 14 have lipophilic characteristics, whereas the inner region 15 of the residues 14 is hydrophilic.

This embodiment has the advantage that in the novel albumin analogs 10, when they are associated with a lipophilic surface, the chain terminals 17 critical for hemocompatibility are facing away from the solution.

Figure 3:
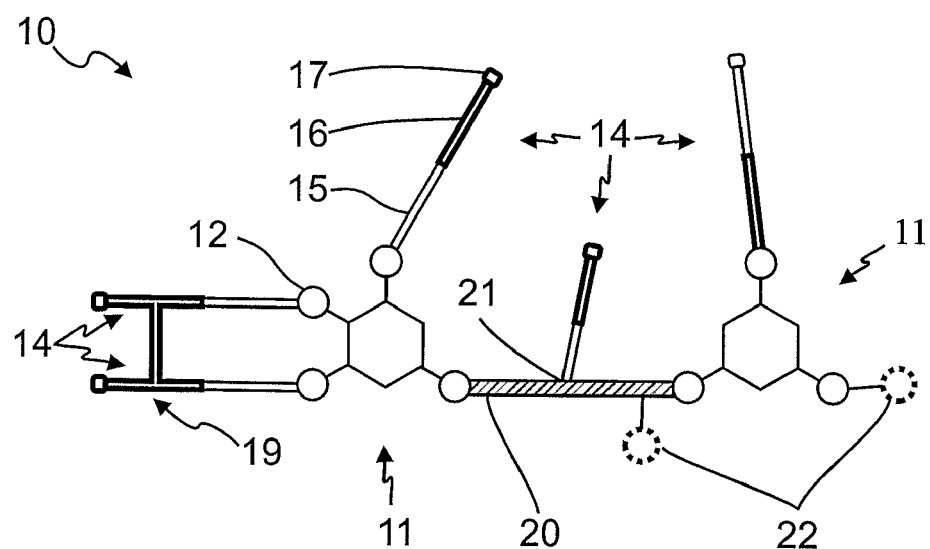
FIG. 3 shows a diagrammatic illustration of a possible embodiment of the novel albumin analogs having two basic structures connected via a bridging unit.

FIG. 3 shows a diagrammatic illustration of a possible embodiment of the novel albumin analogs, in which two basic structures 11 are connected with one another via a bridging unit 20.

As in preceding FIGS. 1 and 2, residues 14 are covalently bound to three-dimensional basic structures 11 via joint regions 12. These residues 14 are divided into an inner region 15 and an outer region 16. Furthermore, the residues 14 have a chain terminal 17.

The division of residues 14 into an inner region 15 and an outer region 16 has the advantage that a greater radius of hydrophilic shielding can be generated; however, at the same time, the linear sequence of lipophilic and hydrophilic portions determines the spatial organization of these molecular moieties. Thus, uniform occupation of a lipophilic surface by hydrophilic molecular moieties in a coating can be achieved more easily.

Here, it is also possible to have single-part residues 14 which, owing to the steric constraint determined by the tight bonding of residues 14 to the basic structure 11, achieve a comparatively rigid molecular geometry with a limited radius of hydrophilic shielding.

Bridges 19, which connect residues 14 with one another, also make a contribution to the steric constraint of the orientation of residues 14.

Furthermore, there is provided between the basic structures 11 a bridging unit 20 to which a branch 21 having a residue 14 is further provided.

At joint regions 12 and at the bridging unit 20, introduced hydrophilic functions 22, for example ionic groups such as carboxylate, phosphate, or sulfonate anions, are depicted.

In addition to their hydrophilicity, these groups make it possible to check the coating quality by means of cationic dyes.

Figure 4:
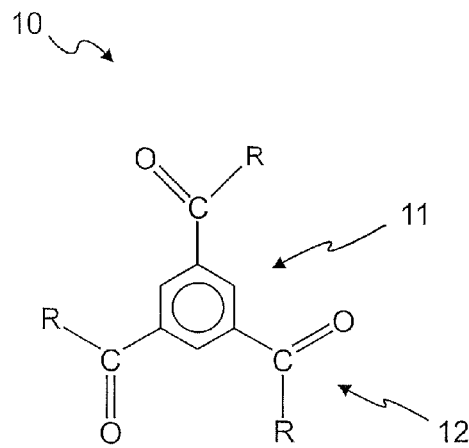
FIG. 4 shows the formula of the basic structure used in the specific embodiments of the novel albumin analogs.

FIG. 4 shows a basic structure 11 of the substances mentioned in the specific exemplary embodiments; which are referred to hereinafter as "Monomer PEO 350", "Monomer PEO 550", and "Dimer PEO 350".

Figure 6:
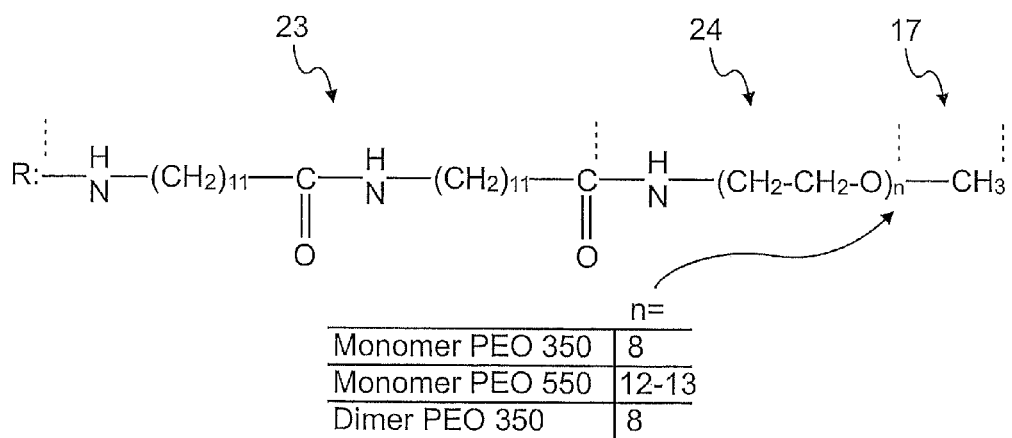
FIG. 6 shows the formula of the residues bound to the basic structures in the specific embodiments of the novel albumin analogs.

Similarly to the diagram shown in FIG. 1, residues denoted by "R" are covalently bound here to a three-dimensional basic structure 11 which consists of a 1,3,5-benzenetricarboxylic acid group, via joint regions 12 which are formed by the acid amide bonds (see FIG. 6 for the formula of the residues).

Figure 5:
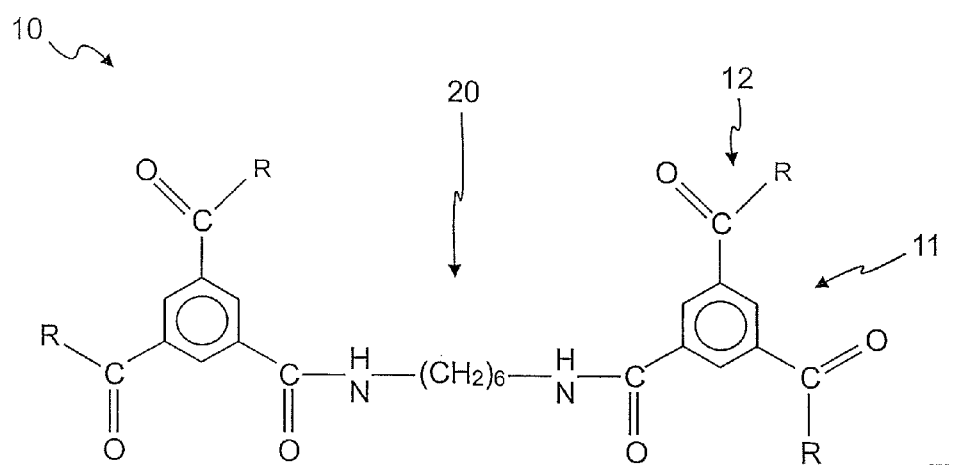
FIG. 5 shows the formula of two basic structures connected by a bridging unit in a specific embodiment of the novel albumin analogs.

FIG. 5 shows the structure of the novel albumin analog, which is referred to hereinafter as "Dimer PEO 350".

This dimer has two basic structures 11 which each consist of one 1,3,5-benzenetricarboxylic acid group and which are connected with one another via a bridging unit 20 which consists of one alkyl chain of the formula $(CH_2)_n$ which has a length of n=6 and which is bound in each case to the basic structures via acid amide bonds acting as joint regions 12, wherein the basic structures 11 each have two residues "R" bound via acid amide bonds acting as joint regions 12.

FIG. 6 shows the basic structure of the bound residues "R" in the specific exemplary embodiments of the novel albumin analogs. These residues have alkyl chains as lipophilic regions 23 and PEO chains as hydrophilic regions 24. The chain terminal 17 on the PEO chains is effected by a methoxyl group.

Here, the substances "Monomer PEO 350" and "Dimer PEO 350" have PEO chains of the formula $(CH_2—CH_2—O)_n$ having a length of n=8 (starting from the dimeric aminoundecanoic acid) and having a molecular weight of about 350 daltons (Da). The substance "Monomer PEO 550" has PEO chains having lengths of n=12-13 (starting from the dimeric aminoundecanoic acid) and having a molecular weight of about 550 daltons (Da).

Figure 7:
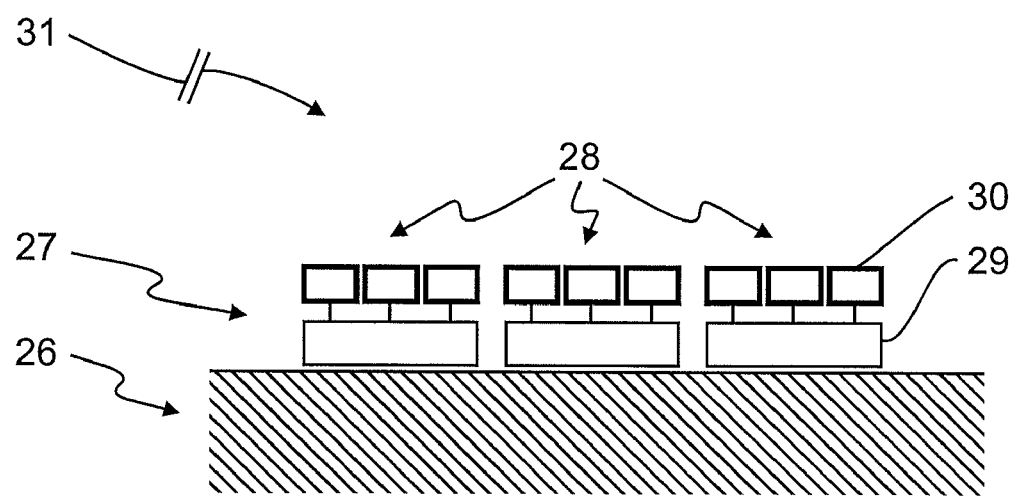
FIG. 7 shows a greatly enlarged diagrammatic section of a surface having a coating according to the invention.

FIG. 7 depicts diagrammatically a greatly enlarged section of a surface 26 which has a coating 27 having the novel albumin analogs 28. The coating 27 is bound to the surface 26 via the lipophilic portions 29 of the novel albumin analogs 28. The coating is in contact with a physiological, aqueous medium 31, for example blood, via the hydrophilic portions 30 of the novel albumin analogs 28 and shields the surface 26 from the medium 31.

The three novel albumin analogs shown in FIGS. 4 to 6 were characterized with respect to their hemocompatibility and antithrombogenic effect and compared with the known Cremophor®EL. The inventor was able to show that the novel albumin analogs are superior to the known Cremophor®EL with respect to their hemocompatibility, more particularly as measured by the platelet number detected in the tested blood after the exposure and by the thromboglobulin concentration, both of which represent a measure of the activation of the immune system.

For this purpose, the three novel albumin analogs cited in FIGS. 4 to 6 were used individually to coat a polycarbonate surface and contacted with blood in a Chandler loop test. Subsequently, the hemocompatibility and antithrombogenicity of the coated surfaces were determined on the basis of several parameters. The controls used were fresh donor blood, uncoated polycarbonate surfaces, and polycarbonate surfaces coated with the known Cremophor®EL.

To determine the hemocompatibility and antithrombogenicity of the coated surfaces, a Chandler loop test was carried out.

Production of the Loops

For the production of the loops, 7 commercially available polycarbonate connectors were initially connected with one another via ⅜" pieces of silicone tubing. For the coating, 1000 ml of aqueous coating solution were pumped around in a loop for 20 minutes at room temperature using 1 m of ⅜" silicone pump tubing with a peristaltic pump at a flow rate of two liters per minute. After the coating, the coating solution was discarded and the coated loops were, without further rinsing, blown with sterile compressed air and dried as a result. After a final drying of four hours at 40° C. in a drying cabinet, the coating process was complete. The coating solutions used had the following compositions:

Table 1: Coating A: 500 mg/liter Cremophor®EL (Caesar+ Loretz GmbH, Hilden) in demineralized water; Coating B: "Monomer PEO 550" dissolved in demineralized water up to saturation point; Coating C: "Monomer PEO 350" dissolved in demineralized water up to saturation point; Coating D: "Dimer PEO 350" dissolved in demineralized water up to saturation point.

Table 2: Coating A: 100 mg/liter Cremophor®EL (Caesar+ Loretz GmbH, Hilden) in demineralized water; Coating B: 100 mg/liter "Dimer PEO 350" in demineralized water; Coating C: 50 mg/liter "Dimer PEO 350" in demineralized water.

Checking the Hemocompatibility of the Coatings

The loops thus treated, having a volume of 36 ml and an inner surface of 150 cm$^2$, were each filled with 20 ml of fresh human blood, as was an uncoated control loop, and rotated in a water bath.

It should be noted here that blood from different donors reacts differently to the contact with potentially hemoincompatible surfaces and the agitation occurring during the test. Thus, in order to achieve highly significant measured values, always blood from the same donor was used in the parallel experiments with different coatings and controls, and the entire experiments were carried out with the blood from five different donors.

After 90 minutes, blood was removed from the loops and these samples were analyzed with regard to certain values.

Table 1 lists the number of intact blood platelets after carrying out the experiments, and also the concentrations of β-thromboglobulin, thrombin-antithrombin, complement SC5b-9, and PMN elastase, for each tubing tested. Listed here are the average values determined from the experiments with the blood from five different donors, and also, in each case, the standard deviation (SD) and the percentage deviation of the average value from the average value from the untreated control blood.

The number of intact blood platelets and concentration of released β-thromboglobulin (iu/ml), both of which are detected in the samples; are the most important parameters here. Here, the first value should be very high; the second, in contrast, should be very low.

It can be seen in table 1 that the number of intact blood platelets for the "Dimer PEO 350" coating (100 mg/l) is distinctly higher than that for the Cremophor®EL coating. The two other substances tested have, in comparison with Cremophor, a slightly increased ("Monomer PEO 550") or virtually similar ("Monomer PEO 350") blood platelet count.

Furthermore, the β-thromboglobulin concentration established in the test with the "Dimer PEO 350" coating is reduced by almost a third compared with the Cremophor®EL coating. This difference is indicative of a substantially better hemocompatibility of the "Dimer PEO 350" coating compared with the Cremophor®EL coating. The two monomeric substances also have here distinctly better values in comparison with Cremophor®EL.

The thrombin-antithrombin value also tested shows that, here too, the "Dimer PEO 350" coating is superior to the Cremophor®EL coating with respect to their hemocompatibility.

TABLE 1

Comparison of "Monomer PEO 550", "Monomer PEO 350", and "Dimer PEO 350" with Cremophor ® EL/500 mg

| | Control blood (fresh donor blood) | Uncoated loop (PC + silicone) | Cremophor ® EL (500 mg/l) | "Monomer PEO 550", saturated | "Monomer PEO 350", saturated | "Dimer PEO 350", saturated |
|---|---|---|---|---|---|---|
| Platelet count ($\times 10^3/\mu l$) (SD) | 219 (32) | 110 (28) | 109 (41) | 119 (49) | 107 (50) | 143 (61) |
| % | 100 | 50 | 50 | 54 | 49 | 65 |
| β-Thromboglobulin (iu/ml) (SD) | 225 (269) | 2948 (1691) | 3567 (2614) | 2627 (1621) | 2283 (1602) | 1610 (1238) |
| % | 100 | 1308 | 1582 | 1165 | 1013 | 714 |
| Thrombin-antithrombin (µg/l) (SD) | 23 (27) | 38 (19) | 29 (10) | 46 (21) | 36 (19) | 31 (18) |
| % | 100 | 163 | 124 | 197 | 153 | 134 |
| Complement SC5b-9 (µg/l) (SD) | 155 (44) | 877 (226) | 1674 (812) | 1948 (920) | 1796 (809) | 1911 (795) |
| % | 100 | 566 | 1080 | 1260 | 1159 | 1233 |
| PMN elastase (µg/l) (SD) | 30 (5) | 63 (15) | 62 (16) | 68 (17) | 75 (29) | 61 (15) |
| % | 100 | 210 | 206 | 226 | 249 | 204 |

(iu: international unit; SD: standard deviation)

From the further results listed in table 1 for complement SC5b-9 and PMN elastase, where lower values in each case indicate better hemocompatibility, it is evident that the three new substances tested have, with respect to these parameters, the same effect as Cremophor®EL or an effect that deviates only slightly from that of Cremophor®EL. It should be mentioned here that the "Dimer PEO 350", with the exception of the complement SC5b-9 value, shows consistently better values than those for the monomers tested.

Furthermore, the results listed in table 2 show that the hemocompatibility of the "Dimer PEO 350" coating can be distinctly increased again by a reduction of the "Dimer PEO 350" concentration used by a half (50 mg/l). Table 2 lists the results of a test in which, similarly to the test represented in table 1, the effectiveness of coating solutions having different defined concentrations of "Dimer PEO 350" were tested in comparison with the effectiveness of a coating solution comprising Cremophor®EL.

Here, it becomes apparent that the coating with "Dimer PEO 350", at the same concentration (mg/l) of coating solution, has almost consistently a better hemocompatibility than the coating with Cremophor®EL.

This tendency can be intensified even more by a further reduction of the "Dimer PEO 350" concentration of the coating solution (mg/l).

The results of the Chandler loop test thus show that the novel albumin analogs having a spatially defined basic structure compared with the known nonionic ester-based substances having a spatially undefined basic structure have improved properties with regard to hemocompatibility and antithrombogenicity.

What is claimed is:

1. A fully synthetic albumin analog having the following structure:

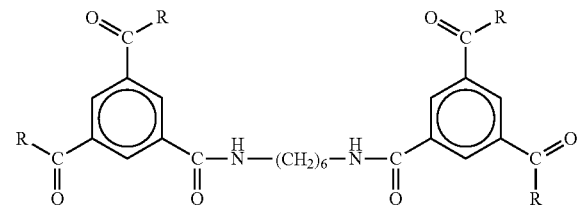

wherein R=

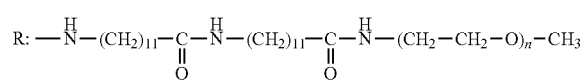

wherein n is an integer from 8 to 13.

2. A hemocompatible coating for surfaces which comes into contact with blood, said coating comprising at least the fully synthetic albumin analog as claimed in claim 1.

3. A medical device having at least one surface which has a hemocompatible coating for surfaces which come into contact with blood, said coating comprising at least the fully synthetic albumin analog of claim 1.

4. The medical device as claimed in claim 3, being a component of devices selected from diposable equipment of a

TABLE 2

Comparison of "Dimer PEO 350", at a low concentration, with Cremophor ®EL (100 mg/l)

| | Control blood (fresh donor blood) | Uncoated loop (PC + silicone) | Cremophor ®EL (100 mg/l) | "Dimer PEO 350" (100 mg/l) | "Dimer PEO 350" (50 mg/l) |
|---|---|---|---|---|---|
| Platelet count ($\times 10^3/\mu l$) (SD) | 242 (34) | 143 (21) | 160 (44) | 183 (43) | 184 (36) |
| % | 100 | 59 | 66 | 76 | 72 |
| β-Thromboglobulin (iu/ml) (SD) | 120 (24) | 1878 (787) | 2501 (868) | 1725 (587) | 1504 (552) |
| % | 100 | 1560 | 2077 | 1432 | 1249 |
| Thrombin-antithrombin (µg/l) (SD) | 2.5 (0.1) | 14.9 (19) | 28.8 (23.7) | 18.9 (10.0) | 9.6 (3.6) |
| % | 100 | 588 | 1139 | 746 | 381 |
| Complement SC5b-9 (µg/l) (SD) | 189 (24) | 996 (340) | 2481 (818) | 2672 (722) | 2481 (715) |
| % | 100 | 527 | 1312 | 1413 | 1312 |
| PMN elastase (µg/l) (SD) | 36 (5) | 71 (8) | 79 (12) | 77 (12) | 74 (9) |
| % | 100 | 200 | 222 | 217 | 207 |

(iu: international unit; SD: standard deviation)

heart-lung machine, an oxygenator, a catheter, an artificial heart, an artificial kidney, a gas exchange membrane, or a vascular prosthesis.

5. The medical device as claimed in claim 3, wherein the surface comprises a material which is selected from polycarbonate, polyethylene, polypropylene, polymethylpentene, polyurethane, polyester, silicone, hard or soft polyvinyl chloride, copolymers, acrylonitrile butadiene styrene copolymer, ethylene propylene (diene) copolymer, or a combination thereof.

* * * * *